United States Patent [19]

Amano et al.

[11] 4,436,939
[45] Mar. 13, 1984

[54] PROCESS FOR PRODUCING 1-(P-PRENYLPHENYL)ETHANOL

[75] Inventors: Takehiro Amano, Urawa; Kensei Yoshikawa, Kitamoto; Tatsuhiko Sano; Yutaka Ohuchi, both of Ohmiya; Michihiro Ishiguro, Kurashiki; Manzo Shiono, Kurashiki; Yoshiji Fujita, Kurashiki; Takashi Nishida, Kurashiki, all of Japan

[73] Assignees: Taisho Pharmaceutical Co., Ltd., Tokyo; Kuraray Co., Ltd., Okayama, both of Japan

[21] Appl. No.: 411,481

[22] Filed: Aug. 25, 1982

[30] Foreign Application Priority Data

Aug. 26, 1981 [JP] Japan ................................ 56-134778

[51] Int. Cl.³ .............................................. C07C 33/28
[52] U.S. Cl. .................................... 568/813; 568/715
[58] Field of Search ................................ 568/715, 813

[56] References Cited

U.S. PATENT DOCUMENTS

| 2,921,940 | 1/1960 | Ramsden | 568/813 |
| 3,856,867 | 12/1974 | Ramsden | 568/813 |
| 4,251,543 | 2/1981 | Amano et al. | 424/317 |

FOREIGN PATENT DOCUMENTS

| 43-27214 | 11/1968 | Japan | 568/813 |
| 50-157306 | 12/1975 | Japan | 568/813 |
| 54-154759 | 12/1979 | Japan | 568/813 |

OTHER PUBLICATIONS

Jones, "J. Organic Chemistry", vol. 35, No. 6, pp. 1777–1781, (1970).

Primary Examiner—Werren B. Lone
Attorney, Agent, or Firm—Wenderoth, Lind & Ponack

[57] ABSTRACT

A process for producing 1-(p-prenylphenyl)ethanol, which comprises reacting p-chloroprenylbenzene with magnesium at a temperature between 100° C. and 150° C. to form a Grignard reagent, and then reacting it with acetaldehyde.

9 Claims, No Drawings

PROCESS FOR PRODUCING 1-(P-PRENYLPHENYL)ETHANOL

This invention relates to a novel and improved process for producing 1-(p-prenylphenyl)ethanol.

1-(p-Prenylphenyl)ethanol is a known compound useful as a synthesis intermediate for 2-(p-prenylphenyl) propionic acid which has excellent anti-inflammatory and analgesic activities and reduced gastrointestinal action. It is known that 1-(p-prenylphenyl)ethanol can be produced by reacting a starting p-haloacetophenone ketal such as 2-(p-bromophenyl)-2-methyl-1,3-dioxolane with magnesium in accordance with the following scheme to prepare a Grignard reagent, reacting it with a prenyl halide, subjecting the resulting 2-methyl-2-(p-prenylphenyl)-1,3-dioxolane to acid hydrolysis to form p-prenylacetophenone, and reducing it with a metal hydride such as sodium borohydride or lithium aluminum hydride (see U.S. Pat. No. 4,251,543).

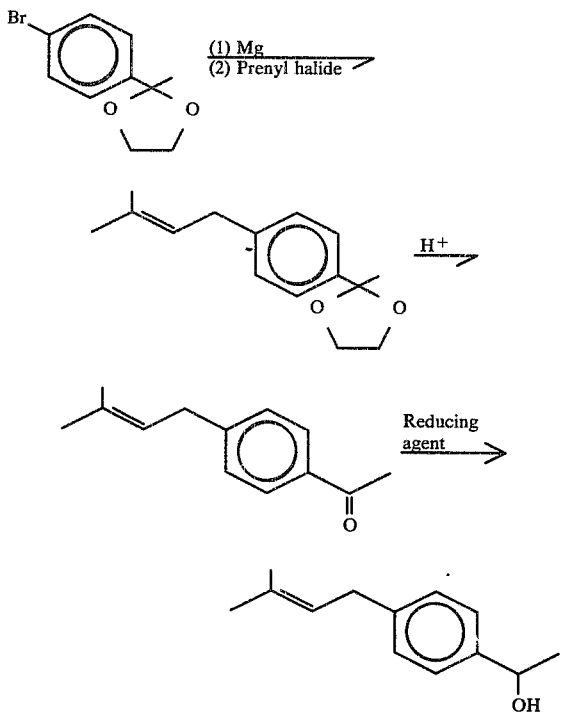

The method for producing 1-(p-prenylphenyl)ethanol shown above has the defect that the starting 2-(p-bromophenyl)-2-methyl-1,3-dioxolane is expensive because it is produced through acetylation of bromobenzene and ketalization, and that the operation is complex because a large amount of a crystalline by-product forms during the Grignard reaction.

We studied a useful method of producing 1-(p-prenylphenyl)ethanol from an industrially more easily available material through a shorter route. As a result, we hit upon an idea of reacting a Grignard reagent, obtained by the reaction of p-chloroprenylbenzene reagent with metallic magnesium, with acetaldehyde, and experimentally performed this reaction.

As regards the preparation of a Grignard reagent from p-chloroprenylbenzene with metallic magnesium, Lee B. Jones et al. reported that they prepared the Grignard reagent in tetrahydrofuran in the same way as in the preparation of a Grignard reagent from bromobenzene and metallic magnesium (by reacting bromobenzene with 1 atomic equivalent of metallic magnesium in the ether solvent in accordance with a customary method). [J. Org. Chem., Vol. 35, No. 6, 1777-1781 (1970)].

Our investigations have shown however that when p-chloroprenylbenzene is reacted with 1 atomic equivalent of metallic magnesium in accordance with an ordinary Grignard reagent preparing method in tetrahydrofuran solvent under reflux at about 70° C., the rate of the reaction is very slow, and the conversion of p-chloroprenylbenzene to the Grignard reagent is extremely low (see Comparative Example 1 given hereinafter).

Further investigations we conducted in order to solve the aforesaid problem have led to the discovery that when p-chloroprenylbenzene and metallic magnesium are heated together at a temperature between 100° C. and 150° C., preferably at a temperature between 110° C. and 130° C., the reaction between them proceeds very smoothly and effectively and the Grignard reagent is formed with good selectivity, and that the reaction of the Grignard reagent with acetaldehyde gives 1-(p-prenylphenyl)ethanol in good yields.

According to this invention, there is provided a novel and industrially advantageous process for producing 1-(p-prenylphenyl)ethanol, which comprises reacting p-chloroprenylbenzene with magnesium at a temperature between 100° C. and 150° C. to form a Grignard reagent, and then reacting it with acetaldehyde.

The reaction of preparing the Grignard reagent from p-chloroprenylbenzene and metallic magnesium is carried out preferably in a solvent. Suitable solvents are those which are usually employed in the preparation of Grignard reagents, and examples include ethers such as tetrahydrofuran, tetrahydropyran, diethyl ether, diisopropyl ether and 1,2-dimethoxyethane. Tetrahydrofuran is especially preferred. This reaction is carried out by using 0.8 to 1.5 atomic equivalents, preferably 1.0 to 1.4 atomic equivalents, of metallic magnesium based on p-chloroprenylbenzene as in the usual preparation of Grignard reagents.

In order to perform the reaction of p-chloroprenylbenzene and magnesium in such proportions smoothly with a high conversion and selectivity, it is critical to use such higher reaction temperatures (i.e., at least 100° C.) than the reaction temperatures heretofore used in Grignard reagent preparation. Lower temperatures have been found to be unable to give feasible rates of reaction. On the other hand, temperatures exceeding 150° C. may increase side-reactions and are not desirable. From the molecular structure of p-chloroprenylbenzene, it is unexpected that it will react with metallic magnesium at a temperature of 100° C. to 150° C. to give the corresponding Grignard reagent with a good selectivity without substantially causing undesirable side-reactions such as the isomerization of the double bond at the side chain of p-chloroprenylbenzene.

In starting the reaction of p-chloroprenylbenzene with magnesium, it is preferred to activate magnesium by adding a small amount of at least one of iodine, ethyl bromide, ethylenedibromide, etc. In order to perform the Grignard reagent-forming reaction at the aforesaid reaction temperatures, i.e., 100° C. to 150° C., preferably 110° C. to 130° C., there can be used, for example, a method which comprises performing the reaction under pressure in an autoclave, or a method which comprises performing the reaction in a very much reduced amount of the solvent, for example using tetrahydrofuran in an amount of about 0.1 to 1.0 part by weight per part by weight of p-chloroprenylbenzene.

The Grignard reagent thus prepared from p-chloroprenylbenzene and metallic magnesium is then reacted with acetaldehyde. Prior to this reaction, the Grignard reagent needs not to be isolated from the reaction mixture, but can be reacted as such with acetaldehyde. The reaction of the Grignard reagent with acetaldehyde is carried out at a temperature of generally between about −40° C. and about 20° C., preferably between about 0° C. and about 10° C. The amount of acetaldehyde is generally about 1 mole or slightly larger, preferably up to about 1.5 moles, per mole of p-chloroprenylbenzene used in the preparation of the Grignard reagent. Under these conditions, the reaction between the Grignard reagent and acetaldehyde proceeds very rapidly, and so long as temperature control is possible, the reaction can be terminated almost instantaneously, for example, in less than several minutes. In industrial practice, a suitable length of time is selected from periods of, for example, up to about 24 hours by considering the ease of removing the heat. After the above-mentioned reaction with acetaldehyde, the reaction mixture is treated in a customary manner, for example treated with an acidic aqueous solution such as an aqueous solution of acetic acid, dilute sulfuric acid or dilute hydrochloric acid or an aqueous solution of ammonium chloride, thereby giving 1-(p-prenylphenyl)ethanol.

The resulting 1-(p-prenylphenyl)ethanol can be separated from the reaction mixture, and purified, by methods known per se, for example extraction, distillation and chromatography.

The p-chloroprenylbenzene used as a starting material in the process of this invention can be easily obtained in high yields by, for example, reacting p-dichlorobenzene with metallic magnesium to form a Grignard reagent and reacting it with a prenyl halide.

Since p-dichlorobenzene is produced industrially in quantities at low cost in order to use it for production of insecticides, etc., the process of this invention which can give 1-(p-prenylphenyl)ethanol substantially in two steps starting from p-dichlorobenzene is very significant from an industrial viewpoint.

The reaction of preparing the Grignard reagent from p-dichlorobenzene and metallic magnesium can be effected by methods known per se, preferably in a solvent. Suitable solvents used in the reaction are ethers such as tetrahydrofuran, tetrahydropyran, diethyl ether, diisopropyl ether and 1,2-dimethoxyethane. Tetrahydrofuran is especially preferred. The reaction temperature is not critical, but generally temperatures of about 40° C. to about 90° C., especially 50° C. to 70° C., are suitable. In starting the reaction, magnesium can be effectively activated by adding a small amount of at least one of iodine, ethyl bromide, ethylenedibromide, etc. The amount of metallic magnesium is generally from about 1 atomic equivalent to a slightly larger amount, for example up to about 1.5 atomic equivalents, based on p-dichlorobenzene.

By coupling the resulting Grignard reagent with a prenyl halide, p-chloroprenylbenzene can be obtained. The coupling reaction is carried out at about 0° C. to about 40° C., preferably about 10° C. to about 30° C. Prenyl chloride and prenyl bromide are preferred as the prenyl halide. The amount of the prenyl halide is generally from 1 mole to a slightly larger amount (usually up to about 1.5 moles) per mole of p-dichlorobenzene used to prepare the Grignard reagent. The resulting p-chloroprenylbenzene can be separated from the reaction mixture by any separating method generally employed, such as extraction, distillation or chromatography.

The p-chloroprenylbenzene can also be produced by preparing a Grignard reagent from metallic magnesium and p-bromochlorobenzene instead of p-dichlorobenzene, and reacting it with a prenyl halide in accordance with the above-mentioned method. In view of availability and cost, the use of p-dichlorobenzene is advantageous in commercial practice. When p-bromochlorobenzene is used instead of p-dichlorobenzene, it can be reacted with metallic magnesium to form a Grignard reagent and then the Grignard reagent can be reacted with a prenyl halide in the same way as in the case of using p-dichlorobenzene except that preferably the Grignard reagent is prepared at a temperature of about 10° C. to about 90° C., particularly 20° C. to 70° C.

As described in the above-cited U.S. Pat. No. 4,251,543, the 1-(p-prenylphenyl)ethanol produced by the process of this invention can be converted to 2-(p-prenylphenyl)propionic acid useful as an analgesic anti-inflammatory agent by treating it with a halogenating agent such as thionyl chloride, phosphorus trichloride and phosphorus tribromide to form a 1-halo-1-(p-prenylphenyl)ethane, cyanating it with a metal cyanide such as sodium cyanide or copper cyanide to form 2-(p-prenylphenyl)-propionitrile, and then hydrolyzing it, or reacting the 1-halo-1-(p-prenylphenyl)ethane with metallic magnesium to form a Grignard reagent and then reacting it with carbon dioxide.

The following examples illustrate the present invention in greater detail.

EXAMPLE 1

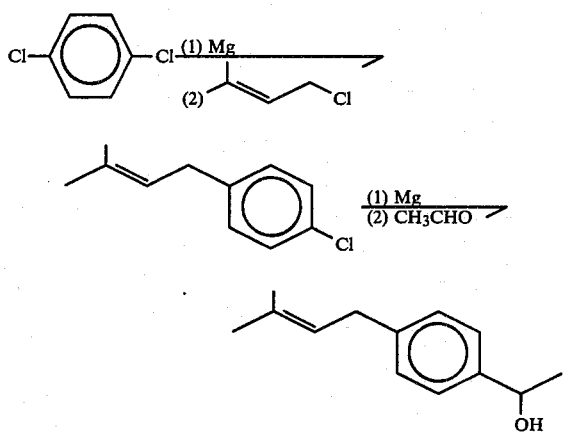

(A) Under a nitrogen atmosphere, 58.3 g of magnesium turnings, 800 ml of tetrahydrofuran and about 0.1 g of iodine were put in a flask. When 2 ml of ethyl bromide was added while stirring the above materials, coloration by iodine disappeared and the temperature of the contents of the flask rose. While tetrahydrofuran was refluxed, a solution of 294 g of p-dichlorobenzene in 2 liters of tetrahydrofuran was added dropwise over the course of about 4 hours. After the addition, the mixture was stirred for 2 hours, and cooled to room temperature. Then, a solution of 271.7 g of prenyl chloride in 800 ml of tetrahydrofuran was added dropwise at 15° C. to 20° C. over about 4 hours. After the addition, the reaction mixture was left to stand overnight at room temperature. Then, 2 liters of a 10% by weight aqueous solution of ammonium chloride was added, and the mixture was separated into an organic layer and an aqueous layer. The aqueous layer was extracted with 300 ml of diethyl ether. The diethyl ether layer was combined with the organic layer previously separated, and washed with water, dried, concentrated and distilled to give 222.3 g (yield 61.6%) of p-chloroprenylbenzene having a boiling point of 64° C. to 65.5° C./0.38 mmHg. The nuclear magnetic resonance spectrum of the product was as follows. (The chemical shifts are expressed in δ (ppm) when hexamethylsiloxane (HMS) is used as a standard.)

$^1$H NMR (CDCl$_3$): δ 1.66 (6H, s), 3.23 (2H, d, J=7.5 Hz), 5.21 (1H, t, J=7.5 Hz), and 6.94–7.26 (4H, m).

(B) Under a nitrogen atmosphere, 9.6 g of magnesium turnings, 30 ml of tetrahydrofuran and about 50 mg of iodine were put in a flask. With stirring, 2 ml of ethyl bromide was added, whereupon coloration by iodine disappeared. With stirring, the mixture was heated and maintained at 110° C. to 120° C., and 60 g of p-chloroprenylbenzene was added. During the reaction, 20 ml of tetrahydrofuran was further added. After continuing the reaction for 4.5 hours, the reaction mixture was cooled to room temperature, and 200 ml of tetrahydrofuran was added. A solution of 22.0 g of acetaldehyde in 30 ml of tetrahydrofuran was added at 5° C. to 10° C. over the course of about 2 hours. After the addition, the mixture was stirred for 1 hour, and then 400 ml of a 10% by weight aqueous solution of ammonium chloride was added. The mixture was separated into an organic layer and an aqueous layer. The aqueous layer was extracted with 30 ml of diethyl ether. The diethyl ether layer was combined with the organic layer previously separated and washed with water, dried, concentrated and distilled to give 47.3 g (yield 74.9%) of 1-(p-prenylphenyl)ethanol having a boiling point of 108° C. to 110° C./0.5 mmHg. The nuclear magnetic resonance spectrum of the product was as follows. (The chemical shifts are expressed in δ (ppm) when hexamethylsiloxane is used as a standard.)

$^1$H NMR (CDCl$_3$): δ 1.36 (3H, d, J=6.5 Hz), 1.67 (6H, s), 2.26 (1H, s), 3.25 (2H, d, J=7.5 Hz), 4.73 (1H, q, J=6.5 Hz), 5.25 (1H, t, J=7.5 Hz), and 7.0–7.3 (4H, m).

EXAMPLE 2

Magnesium turnings (9.6 g), 250 ml of tetrahydrofuran and about 50 mg of iodine were put in an autoclave purged with nitrogen. With stirring, 2 ml of ethyl bromide was added, and then, 60 g of p-chloroprenylbenzene was added. The mixture was heated and maintained at 110° C. to 120° C. for 5 hours. The reaction mixture was cooled to room temperature, and transferred to a 500 ml three-necked flask. In an atmosphere of nitrogen, a solution of 22.0 g of acetaldehyde in 30 ml of tetrahydrofuran was added dropwise at 5° C. to 10° C. over the course of about 2 hours. After the addition, the mixture was stirred for 1 hour, and then 400 ml of a 10% by weight aqueous solution of ammonium chloride was added. The mixture was separated into an organic layer and an aqueous layer. The aqueous layer was extracted with 30 ml of diethyl ether. The diethyl ether was combined with the organic layer previously separated, and washed with water, dried, concentrated and distilled to give 45.2 g (yield 71.6%) of 1-(p-prenylphenyl)ethanol.

EXAMPLE 3 p-Chloroprenylbenzene was produced in the same way as in Example 1 except that 413.4 g of prenyl bromide was used instead of 271.7 g of prenyl chloride. The amount of p-chloroprenylbenzene obtained was 245.8 g (yield 68.1%). Using 60 g of the resultant p-chloroprenylbenzene, 1-(p-prenylphenyl)ethanol was produced in the same way as in Example 1. The amount of 1-(p-prenylphenyl)ethanol obtained was 47.5 g (yield 75.2%).

EXAMPLE 4

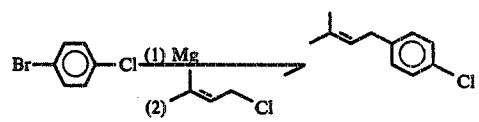

Under nitrogen atmosphere, 55.1 g of magnesium turnings, 800 ml of tetrahydrofuran, and about 0.1 g of several pieces of iodine were put in a flask. With stirring, 2 ml of ethyl bromide was added, whereupon coloration by iodine disappeared. Then, a solution of 361.7 g of p-bromochlorobenzene in 2 liters of tetrahydrofuran was added dropwise at such a speed that the reaction temperature was maintained at 25° C. to 30° C. After the addition, the mixture was further stirred for 1 hour, and cooled to about 20° C. A solution of 256.8 g of prenyl chloride in 800 ml of tetrahydrofuran was added dropwise at 15° C. to 20° C. over the course of about 4 hours. After the addition, the mixture was left to stand overnight at room temperature. Two liters of a 10% by weight aqueous solution of ammonium chloride were added, and the mixture was separated into an organic layer and an aqueous layer. The aqueous layer was extracted with 300 ml of diethyl ether. The diethyl ether layer was combined with the organic layer previously separated, and washed with water, dried, concentrated, and distilled to give 218.3 g (yield 64.0%) of p-chloroprenylbenzene.

COMPARATIVE EXAMPLE 1

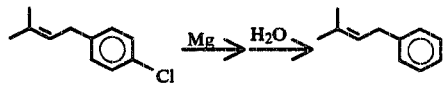

The following comparative experiment was conducted in order to demonstrate the superiority (high conversion) of the Grignard reagent preparation in accordance with the process of this invention from p-chloroprenylbenzene and magnesium to a conventional process.

(A) Conventional process (reaction temperature; the refluxing temperature of tetrahydrofuran, i.e. about 70° C.):

Under nitrogen atmosphere, 0.8 g of magnesium turnings, 10 ml of tetrahydrofuran and about 5 mg of iodine were put in a flask. With stirring, 0.2 ml of ethyl bromide was added, whereupon coloration by iodine disappeared. While tetrahydrofuran was refluxed with stirring, a solution of 6 g of p-chloroprenylbenzene in 20 ml of tetrahydrofuran was added, and the reaction was carried out for 5 hours. After the reaction, the reaction mixture was cooled to room temperature, and poured into 40 ml of a 10% aqueous solution of ammonium chloride to hydrolyze the Grignard reagent. The product was analyzed by gas chromatography. It was found that in the above Grignard reagent producing reaction, the conversion of p-chloroprenylbenzene was 9.0%.

(B) Process of the invention (reaction temperature: 110° C.–130° C.):

Under nitrogen atmosphere, 0.8 g of magnesium turnings, 3 ml of tetrahydrofuran and about 5 mg of iodine were put in a flask. With stirring, 0.2 ml of ethyl bromide was added, whereupon coloration by iodine disappeared. While tetrahydrofuran was refluxed with stirring, a solution of 6 g of p-chloroprenylbenzene in 2 ml of tetrahydrofuran was added, and the reaction was carried out at 110° C. to 130° C. for 5 hours. After the reaction, the reaction mixture was cooled to room temperature, and poured into 40 ml of a 10% by weight aqueous solution of ammonium chloride to hydrolyze the Grignard reagent. Analysis of the product by gas chromatography showed that in the Grignard reagent producing reaction, the conversion of p-chloroprenylbenzene was 95.6%.

REFERENTIAL EXAMPLE

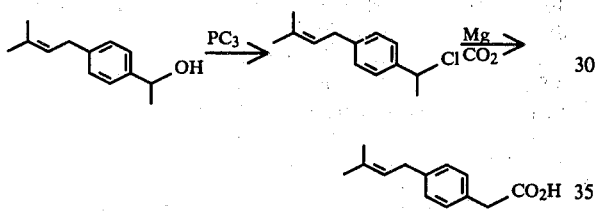

166 g of 1-(p-prenylphenyl)ethanol was dissolved in a mixture of 870 ml of acetone and 34.5 g of pyridine. While the solution was maintained at 0° C., 60.1 of phosphorus trichloride was added over the course of about 2 hours. The mixture was stirred at room temperature for 2 hours. Acetone was distilled off, and n-hexane and cold water were added to the mixture. The n-hexane layer was washed successively with a 1.6% aqueous solution of sodium hydroxide and water, dried and concentrated to give 174.6 g of 1-chloro-1-(p-prenylphenyl)ethane.

In an atmosphere of nitrogen, 81.3 g of magnesium turnings, 983 ml of tetrahydrofuran and about 0.2 g of iodine were mixed, and 2 ml of ethyl bromide was added to activate magnesium. A solution of 174.6 g of the 1-chloro-1-(p-prenylphenyl)ethane obtained as above in 170 ml of tetrahydrofuran was added dropwise at a reaction temperature of 20° C. to 25° C. over the course of 4 hours. After the addition, the mixture was stirred at the same temperature for 1 hour. The reaction mixture was then cooled to a temperature between −20° C. and −10° C., and carbon dioxide gas was blown into it at the same temperature until no exotherm was noted. The reaction mixture was warmed to room temperature, and poured into dilute hydrochloric acid, followed by extraction with diisopropyl ether. A 2 N aqueous solution of sodium hydroxide was added to the diisopropyl ether extract, and the mixture was stirred and allowed to stand and separate. The resulting aqueous layer was washed three times with n-hexane, and then acidified with 2 N hydrochloric acid. The resulting mixture was then extracted with diisopropyl ether. The extract was washed with water and a small amount of an aqueous solution of sodium bicarbonate, dried, concentrated and then subjected to molecular distillation to give 100 g of 2-(p-prenylphenyl)propionic acid.

What we claim is:

1. A process for producing 1-(p-prenylphenyl)ethanol, which comprises reacting p-chloroprenylbenzene with magnesium at a temperature between 100° C. and 150° C. to form a Grignard reagent, and then reacting said Grignard reagent with acetaldehyde at a temperature between −40° C. and 20° C.

2. The process of claim 1 wherein the reaction of p-chloroprenylbenzene with magnesium is carried out at a temperature between 100° C. and 130° C.

3. The process of claim 1 wherein magnesium is used in an amount of 0.8 to 1.5 atomic equivalents, based on p-chloroprenylbenzene.

4. The process of claim 1 wherein the amount of magnesium is 1.0 to 1.4 atomic equivalents based on p-chloroprenylbenzene.

5. The process of claim 1 wherein magnesium is activated with iodine, ethyl bromide, and/or ethylenedibromide.

6. The process of claim 1 wherein the reaction of p-chloroprenylbenzene with magnesium is carried out in the presence of an ether.

7. The process of claim 1 wherein the reaction of p-chloroprenylbenzene with magnesium is carried out in tetrahydrofuran.

8. The process of claim 1 wherein the amount of acetaldehyde is about 1 to about 1.5 moles per mole of p-chloroprenylbenzene.

9. The process of claim 3 wherein the amount of acetaldehyde is about 1 to 1.5 moles per mole of p-chloroprenylbenzene.

* * * * *

UNITED STATES PATENT AND TRADEMARK OFFICE
CERTIFICATE OF CORRECTION

PATENT NO. : 4,436,939
DATED : March 13, 1984
INVENTOR(S) : TAKEHIRO AMANO ET AL.

It is certified that error appears in the above-identified patent and that said Letters Patent is hereby corrected as shown below:

Column 7, line 30, change "PC₃" to -- PCl₃ -- ;

Column 7, line 35, change the formula " 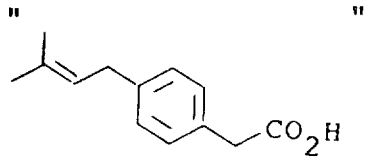 "

to --  --.

Signed and Sealed this

Second Day of October 1984

[SEAL]

Attest:

Attesting Officer

GERALD J. MOSSINGHOFF

Commissioner of Patents and Trademarks